US012329763B2

(12) United States Patent
Liu et al.

(10) Patent No.: US 12,329,763 B2
(45) Date of Patent: *Jun. 17, 2025

(54) COMPOSITION OF LANOSTEROL PRODRUG COMPOUND, PREPARATION METHOD THEREFOR AND USE THEREOF

(71) Applicant: Guangzhou Ocusun Ophthalmic Biotechnology Co., Ltd., Guangzhou (CN)

(72) Inventors: Yizhi Liu, Guangzhou (CN); Yandong Wang, Guangzhou (CN); Xiaolin Li, Shanghai (CN); Zhi Luo, Shanghai (CN); Haiying He, Shanghai (CN)

(73) Assignee: Guangzhou Ocusun Ophthalmic Biotechnology Co., Ltd., Guangzhou (CN)

( * ) Notice: Subject to any disclaimer, the term of this patent is extended or adjusted under 35 U.S.C. 154(b) by 941 days.

This patent is subject to a terminal disclaimer.

(21) Appl. No.: 17/435,668

(22) PCT Filed: Mar. 4, 2020

(86) PCT No.: PCT/CN2020/077765
§ 371 (c)(1),
(2) Date: Sep. 1, 2021

(87) PCT Pub. No.: WO2020/177714
PCT Pub. Date: Sep. 10, 2020

(65) Prior Publication Data
US 2022/0133744 A1    May 5, 2022

(30) Foreign Application Priority Data

Mar. 4, 2019   (CN) .......................... 201910161146.7

(51) Int. Cl.
| | |
|---|---|
| A61K 31/575 | (2006.01) |
| A61K 47/02 | (2006.01) |
| A61K 47/10 | (2017.01) |
| A61K 47/18 | (2017.01) |
| A61K 47/26 | (2006.01) |
| A61K 47/32 | (2006.01) |
| A61K 47/34 | (2017.01) |
| A61K 47/36 | (2006.01) |
| A61K 47/38 | (2006.01) |
| A61P 27/12 | (2006.01) |

(52) U.S. Cl.
CPC ............ A61K 31/575 (2013.01); A61K 47/02 (2013.01); A61K 47/10 (2013.01); A61K 47/183 (2013.01); A61K 47/26 (2013.01); A61K 47/32 (2013.01); A61K 47/34 (2013.01); A61K 47/36 (2013.01); A61K 47/38 (2013.01); A61P 27/12 (2018.01)

(58) Field of Classification Search
CPC .... A61K 31/575; A61K 47/10; A61K 47/183; A61K 47/02; A61K 47/26; A61K 47/32; A61K 47/34; A61K 47/36; A61K 47/38; A61P 27/12

See application file for complete search history.

(56) References Cited

U.S. PATENT DOCUMENTS

| 8,685,945 B2 * | 4/2014 | Ketelson | ................ A61K 31/08 |
| | | | 514/54 |
| 10,738,076 B2 * | 8/2020 | Liu | ....................... C07J 41/0055 |

FOREIGN PATENT DOCUMENTS

| CN | 106074568 A | 11/2016 | |
| WO | WO-2016029199 A1 * | 2/2016 | ........... A61K 31/573 |
| WO | 2018036522 A1 | 3/2018 | |
| WO | WO-2018137683 A1 * | 8/2018 | ........... A61K 31/575 |
| WO | WO-2020020306 A1 * | 1/2020 | ........... A61K 31/573 |

OTHER PUBLICATIONS

Santvliet et al., "Determinants of Eye Drop Size", 2004, Survey of Ophthalmology, 49, pp. 197-213 (Year: 2004).*
Moore et al., "An objective assessment of the variability in No. of drops per bottle of glaucoma medication", 2017, BMC Ophthalmology, 17, pp. 1-7 (Year: 2017).*
International Search Report and Written Opinion for PCT/CN2020/077765 dated May 27, 2020, 11 pages, English translation of ISR only.
Chinese Application No. 201910161146.7 filed Mar. 4, 2019, with English translation, 41 pages.

* cited by examiner

*Primary Examiner* — Jeffrey H Murray
*Assistant Examiner* — Madeline E Braun
(74) *Attorney, Agent, or Firm* — Sheppard Mullin Richter & Hampton LLP (57) ABSTRACT

A composition includes a compound as shown in formula (I). The compound and composition can be used in the preparation of a drug for treating ophthalmic diseases.

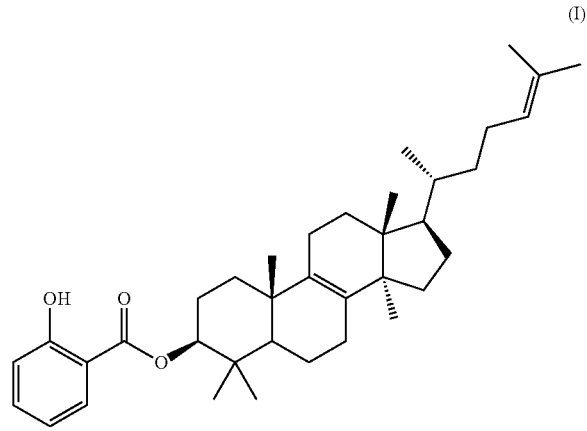

18 Claims, 4 Drawing Sheets

COMPOSITION OF LANOSTEROL PRODRUG COMPOUND, PREPARATION METHOD THEREFOR AND USE THEREOF

RELATED APPLICATIONS

This application is a U.S. National Stage Application under 35 U.S.C. § 371 of International Application No. PCT/CN2020/077765, filed Mar. 4, 2020, which claims priority to Chinese Patent Application No. CN201910161146.7, filed Mar. 4, 2019, the contents of which are incorporated to the present disclosure by reference.

TECHNICAL FIELD

The present disclosure relates to a composition comprising a compound as shown in formula (I) and a preparation method therefor, and a use thereof in the preparation of a medicament for treating ophthalmic diseases.

BACKGROUND

Cataract is a disease of the eye which occurs in the lens in the eyeball and the lens turbidity is collectively called cataract. Aging, heredity, metabolic abnormality, trauma, radiation, poisoning and local malnutrition can cause damage to the lens capsule resulting in increase of permeability and lose of barrier function, or cause metabolic disorders of the lens resulting in denaturation of lens protein and formation of turbidity. If the lens of the eyeball changes from transparence to opacity and has an impact on the sunlight received by eyes, it will affect the eyesight of the eyes. When the degree of turbidity of eyeball is light, the effect on vision is lighter, but as the degree of turbidity gradually deepens, the visual acuity will increase, and severe cases will lead to blindness. Cataract is one of the most common eye diseases leading to blindness and it is a major cause of blindness. Since the mechanism of cataract formation is still unclear, no breakthrough has been made in drug therapy. Therefore, currently the only effective treatment is surgical treatment.

Although the continuous improvement of cataract surgery has provided great assistance to the treatment of cataract, the cure rate of surgical treatment is still far below the incidence rate, and there is the possibility of serious complications. On the other hand, the cost of surgical treatment of cataract is very high, and even in developed countries, cataract imposes a huge burden on the medical insurance system. Therefore, the prevention and treatment with usage of drugs play a decisive role. At present, therapeutic drugs available clinically for cataract include: 1, aldose reductase inhibitors, such as cataline (Catalin, Kary Uni, prifenoxinesodium), phacolysis, bendazac L-lysine, etc.; 2, anti-oxidative damage drugs, such as glutathione, taurine, aspirin, etc.; 3, nutrient metabolism drugs, such as vitamins, carotenoids, etc.; 4, chinese herbal compound including Shihu Yeguang Pill, Qiju Dihuang Pill, Shijueming San and so on. It has been confirmed by long-term clinical trials that these drugs for the treatment of cataract can only delay the deterioration of cataract, but can not reverse the condition to treat cataract.

Meanwhile, as China begins to enter an aging society, the number of cataract patients is increasing, and the demand for cataract drugs will become more urgent. Therefore, new varieties of ophthalmic external anti-cataract drugs with safety, good curative effect, strong intraocular penetration and stable nature are needed clinically.

Lanosterol is an amphiphilic molecule enriched in the lens which is synthesized from lanosterol synthase (LSS) through a key cyclization reaction of the cholesterol synthesis pathway and can reduce the abnormal aggregation of lens proteins and make it regularly rearranged to restore crystal transparency. Studies have shown that lanosterol synthase can be detected in the lens. Furthermore, in the Shumiya cataract rat study, a specific combination of homozygous mutations of lanosterol synthase and farnesyl diphosphate farnesyltransferase 1 (FDFT1) can alleviate cholesterol levels in the lens and cause cataracts. Meanwhile, our recent studies have found that lanosterol can significantly reduce pre-formed lens protein aggregates in vitro at the cellular level. It has also been confirmed that lanosterol can reverse the condition of cataract and bring about clarification and transparency of the lens in vivo. This result has recently been published in *Nature* and attracted worldwide attention and it is a new molecule for the prevention and treatment of cataract.

Lanosterol

Kary Uni eye drops is a medicine produced by Santen Pharmaceutical Co., Ltd in Japan for the treatment of early senile cataract and the structural formula of its active ingredient is showed below:

Content of the Present Invention

The present disclosure provides a composition comprising a compound of formula (I) and an excipient, (I)

In some embodiments of the present disclosure, the content of the compound of formula (I) is 0.1-0.3%.

In some embodiments of the present disclosure, the excipient is one or more selected from solubilizer, pH modifier, osmotic pressure regulator, surfactant, thickener, humectant, adhesive, suspending agent, dispersant, lubricant and water.

In some embodiments of the present disclosure, the solubilizer is one or more selected from HCl, polyethylene glycol 200 (PEG200), polyethylene glycol 400 (PEG400), glycerin, poloxamer 407, polyethylene oxide (PEO), sulfobutyl-β-cyclodextrin (SBE-β-CD), hydroxypropyl-β-cyclodextrin (HP-β-CD), poloxamer 188, polyvinylpyrrolidone (PVP) and Tween 80.

In some embodiments of the present disclosure, the pH modifier is one or more selected from HCl, Tris-HCl, citric acid buffer and NaOH.

In some embodiments of the present disclosure, the osmotic pressure regulator is one or more selected from phosphate buffered saline (PBS), sodium hyaluronate, dipotassium ethylenediaminetetraacetate (EDTA-$K_2$), disodium ethylenediaminetetraacetate (EDTA-$Na_2$) and amino acid-based pH modifier.

In some embodiments of the present disclosure, the surfactant is one or more selected from Tween 80, Tween 20 and hydrogenated castor oil.

In some embodiments of the present disclosure, the thickener is one or more selected from PEG200, glycerin, PEG400, poloxamer 188, poloxamer 407, PEO, polyoxyethylene castor oil, sodium hyaluronate, sodium carboxymethyl cellulose, methyl cellulose (MC), carboxymethyl cellulose (CMC), hydroxyethyl cellulose (HEC), cellulose acetate phthalate (CAP) and hydroxypropyl methyl cellulose (HPMC E5).

In some embodiments of the present disclosure, the humectant is one or more selected from glycerin, PEG200 and PEG400.

In some embodiments of the present disclosure, the adhesive is one or more selected from poloxamer 407, PEO, PVP, sodium carboxymethyl cellulose, MC, CMC, HEC, CAP and HPMC E5.

In some embodiments of the present disclosure, the suspending agent is one or more selected from sodium carboxymethyl cellulose, MC, CMC, HEC, CAP, and HPMC E5.

In some embodiments of the present disclosure, the dispersant is one or more selected from glycerin, PEG200 and PEG400.

In some embodiments of the present disclosure, the lubricant is one or more selected from glycerin, PEG200 and PEG400.

The present disclosure provides a composition with:

(1) 30.38 mg of the compound of formula (I), 1.971 mL of 0.05 mol/L HCl solution, 1 mg of EDTA-$Na_2$, 0.808 mL of 10% Tween 80 aqueous solution, 11.8 µL of 5N NaOH aqueous solution, and 6.421 mL of water;

(2) 30.38 mg of the compound of formula (I), 0.500 mL of PEG400, 1 ma of EDTA-$Na_2$, 0.1 mL of PBS, 2.009 g of poloxamer 188, and 7.459 mL of water;

(3) 30.38 mg of the compound of formula (I), 0.500 mL of 0.05 mol/L HCl aqueous solution, 0.800 mL of 10% Tween 80 aqueous solution, 0.800 mL of 10% polyoxyethylene castor oil solution, 0.080 mL of glycerin, and 7.818 mL of 0.1% sodium hyaluronate aqueous solution;

(4) 30.38 m2 of the compound of formula (I), 0.500 mL of PEG400, 1.900 g of poloxamer 188, and 7.570 mL of 0.1% sodium hyaluronate solution;

(5) 30.38 mg of the compound of formula (I), 0.400 mL of PEG400, 0.040 mL of Tween 80, 1 mg of EDTA-$K_2$, and 9.529 mL of 0.1% sodium hyaluronate solution;

(6) 10 mg of the compound of formula (I), 500 mg of HP-β-CD, 0.100 mL of Tween 80, 50 mg of PVP, and 9.340 mL of water;

(7) 10 mg of the compound of formula (I), 50 mg of sodium carboxymethyl cellulose, 50 mg of Tween 80, and 9.99 mL of water;

(8) 10 mg of the compound of formula (I), 0.45 g of PEG400, 0.025 g of Tween 80, 0.025 g of PVT, 0.475 g of HP-β-CD, and 8.515 mL of water;

or (9) 30.38 ma of the compound of formula (I), 0.12 g of HPMC E5, 2.05 g of poloxamer P407, 0.16 g of poloxamer P188, and 7.67 mL of water.

In some embodiments of the present disclosure, the composition is an ophthalmic formulation for the treatment of cataract.

In some embodiments of the present disclosure, the ophthalmic formulation is eye drops.

In some embodiments of the present disclosure, the specification of the eye drops is 10 mL.

Technical Effect

The composition of the present disclosure can alleviate cataract symptoms, improve lens transparency and lens GSH-PX activity.

Definition and Description

Unless otherwise specified, the following terms and phrases used herein are intended to have the following meanings. A specific term or phrase should not be considered indefinite or unclear in the absence of a particular definition but should be understood in the ordinary sense. When a trade name appears herein, it is intended to refer to its corresponding commodity or active ingredient thereof.

The intermediate compounds of the present disclosure can be prepared by a variety of synthetic methods known to those skilled in the art, including the specific embodiments listed below, the embodiments formed by their combination with other chemical synthesis methods, and equivalent alternatives known to those skilled in the art, preferred implementations include but are not limited to the embodiments of the present disclosure.

The term "excipient" generally refers to carriers, diluents and/or mediums required to formulate an effective pharmaceutical composition.

The chemical reaction in the specific embodiment of the present disclosure is completed in a suitable solvent, and the solvent must be suitable for the chemical change and the required reagents and materials of the present disclosure. In order to obtain the compound of the present disclosure, it is sometimes necessary for the person skilled in the art to modify or select the synthesis steps or reaction schemes based on the existing embodiments.

The present disclosure will be further described in detail by the following embodiments, but these embodiments are not meant to limit the present disclosure in any way.

All solvents used in the present disclosure are commercially available and can be used without further purification.

The solvents used in the present disclosure are commercially available.

The following abbreviations are used in the present disclosure: PEG400: polyethylene glycol 400; PVP: polyvinylpyrrolidone; HP-β-CD: hydroxypropyl β-cyclodextrin.

INSTRUMENTS AND ANALYSIS METHODS

The Main Instruments and Parameters Used in the Process of Preparing Formulations are Shown in Table 1.

TABLE 1

| Instrument name | Instrument model | Parameter |
| --- | --- | --- |
| Magnetic stirrer | IKA-C-MAGHS 10 IKA-RET Basic and 85-2A | Rotation speed range: 0-1700 r/min |
| Micro vortex mixer | XW-80A | 2800 r/min; amplitude: 6 mm |
| Ultrasonic crusher | Covaris ---E220x SCIENTZ-950E, | The parameter range can be adjusted as required |

DETAILED DESCRIPTION OF THE EMBODIMENTS

The following examples further illustrate the present disclosure, but the present disclosure is not limited thereto. The present disclosure has been described in detail herein, and its specific embodiments have also been disclosed, for one skilled in the art, it is obvious to make various modifications and improvements to the embodiments of the present disclosure without departing from the spirit and scope of the present disclosure.

For a better understanding of the content of the present disclosure, it will be further described in combination with the following specific embodiments, but the embodiments are not the limitations of the contents of the present disclosure.

Prescription 1:
  The compound of formula (I): 30.38 mg
  0.05 mol/L HCl solution: 1.971 mL
  EDTA-Na$_2$: 1 mg
  10% Tween 80 aqueous solution: 0.808 mL
  5N NaOH aqueous solution: 11.8 μL
  Water: 6.421 mL
  The specific preparation steps are as follows:
  1.971 mL of 0.05 mol/L HCl solution was added into a glass container containing the compound of formula (I); the resulting mixture was stirred for 15 minutes at 60° C., and subjected to ultrasonic treatment in a water bath for 10 minutes to obtain a heterogeneous suspension; then 1 mg of EDTA-Na$_2$ (dissolved in an appropriate amount of 1×PBS solution) was added thereto, and stirred for 15 minutes at 60° C.; then 0.808 mL of 10% Tween aqueous solution was added, and then stirred for 20 minutes at 60° C.; 11.8 μL of 5N NaOH was then added and stirred for 2 minutes to adjust pH value to 6.9, and a homogeneous suspension was obtained; finally, pure water was added until the total volume reached 10 mL, and the resulting mixture was stirred for 5 minutes to obtain a homogeneous suspension.

Prescription 2:
  The compound of formula (I): 30.38 mg
  PEG400: 0.500 mL
  EDTA-Na$_2$: 1 mg
  PBS: 1 mL
  Poloxamer 188: 2.009 g
  Water: 7.459 mL
  The specific preparation steps are as follows:
  0.5 mL of PEG400 was added into a glass container containing the compound of formula (I); the resulting mixture was stirred for 15 minutes at 60° C., and subjected to ultrasonic treatment in a water bath for 10 minutes to obtain a heterogeneous suspension; then 1 mg of EDTA-Na$_2$ (dissolved in 1 mL of PBS solution) was added thereto, and stirred for 15 minutes at 60° C.; then 2.009 g of poloxamer 188 was added, and then stirred for 2 minutes; finally, pure water was added until the total volume reached 10 mL, and the resulting mixture was stirred overnight at 4° C. to obtain a homogeneous suspension.

Prescription 3:
The compound of formula (I): 30.38 mg
0.05 mol/L HCl aqueous solution: 0.500 mL
10% Tween 80 aqueous solution: 0.800 mL
10% polyoxyethylene castor oil solution: 0.800 mL
Glycerin: 0.080 mL
0.1% sodium hyaluronate solution: 7.818 mL
The specific preparation steps are as follows:
0.5 mL of 0.05 mol/L HCl aqueous solution was added into a glass container containing the compound of formula (I), and vortexed for 2 minutes; then 0.8 mL of 10% Tween 80 solution was added and stirred for 30 minutes at 60° C. to obtain a homogeneous suspension; 0.8 mL of 10% polyoxyethylene castor oil solution and 0.08 mL of glycerin were then added and the mixture was vortexed for 1 minute, and then stirred for 20 minutes at 60° C.; finally, 7.818 mL of 0.1% sodium hyaluronate solution was added, and the mixture was further vortexed for 1 minute, stirred for 20 minutes at 60° C. and subjected to ultrasonic treatment in a water bath for 10 minutes to obtain a homogeneous suspension.

Prescription 4:
The compound of formula (I): 30.38 mg
PEG400: 0.500 mL
Poloxamer 188: 1.900 g
0.1% sodium hyaluronate solution: 7.570 mL
The specific preparation steps are as follows:
0.5 mL of PEG400 was added into a glass container containing the compound of formula (I); the mixture was vortexed for 2 minutes and stirred for 30 minutes at 60° C. to obtain a homogeneous suspension (with large compound particulates); then 1.9 g of poloxamer 188 was added and stirred for 1 minute; then, 4 mL of 0.1% sodium hyaluronate solution was added and vortexed for 1 minute, and then stirred for 40 minutes at 2-8° C. to obtain a homogeneous suspension; finally, 0.1% sodium hyaluronate solution was added until the total volume reached 10 mL; the mixture was further vortexed for 1 minute, and stirred for 20 minutes at 28° C. to obtain a homogeneous suspension.

Prescription 5:
The compound of formula (I): 30.38 mg
PEG400: 0.400 mL
Tween 80: 0.040 mL
EDTA-$K_2$: 1 mg
0.1% sodium hyaluronate solution: 9.529 mL
The specific preparation steps are as follows:
0.4 mL of PEG400 was added into a glass container containing the compound of formula (I); the mixture was vortexed for 2 minutes, and for 30 minutes stirred at 60° C.; then 0.04 mL of Tween 80 was added and stirred for 1 minute to obtain a homogeneous suspension (with large compound particulates); 8 mL of 0.1% sodium hyaluronate solution was added and vortexed for 1 minute, and then stirred for 40 minutes at 60° C.; then 1 mg of EDTA-$K_2$ was added and stirred for 2 minutes until dissolved; finally, 1.529 mL of 0.1% sodium hyaluronate solution was added and vortexed for 1 minute, and stirred for 20 minutes at 60° C. to obtain a homogeneous suspension.

Prescription 6:
The compound of formula (I): 10 mg
HP-β-CD: 500 mg
Tween 80: 0.100 mL
PVP: 50 mg
Water: 9.340 mL The specific preparation steps are as follows:
500 mg of HP-β-CD and 0.100 mL Tween 80 were added into a glass container containing the compound of formula (I), then 9.340 mL of water was added thereto, and the resulting mixture was thoroughly stirred for 50 minutes at 45° C.; then 50 mg of PVP was added and stirred for 2 minutes. Finally, the mixture was subjected to ultrasonic treatment for 20 minutes by using a Covaris ultrasonic crusher to obtain a homogeneous suspension.

Prescription 7:
The compound of formula (I): 10 mg
Sodium carboxymethyl cellulose: 50 mg,
Tween 80: 50 mg,
Water: 9.99 mL
The specific preparation steps are as follows:
50 mg of sodium carboxymethyl cellulose and 50 mg of Tween 80 were added into a glass container containing the compound of formula (I), then 9.99 mL of water was added thereto and stirred for 30 minutes at 45° C.; finally, the mixture was subjected to ultrasonic treatment for 20 minutes by using a Covaris ultrasonic crusher to obtain a homogeneous suspension.

Prescription 8:
The compound of formula (I): 10 mg
PEG400: 0.45 g
Tween 80: 0.025 g
PVP: 0.025 g
HP-β-CD: 0.475 g
Water: 8.515 mL
The specific preparation steps are as follows:
0.45 g of PEG400, 0.025 g of Tween 80 and 0.025 g of PVP were added into a glass container containing the compound of formula (I), and the mixture was stirred at for 15 minutes 45° C.; then 0.475 g of HP-β-CD and 8.515 mL of water was added thereto, and stirred for 15 minutes at 45° C.; finally, the mixture was subjected to ultrasonic treatment for 20 minutes by using a Covaris ultrasonic crusher to obtain a homogeneous suspension.

Prescription 9:
The compound of formula (I): 30.38 mg
HPMC E5: 0.12 g,
Poloxamer P407: 2.05 g,
Poloxamer P188: 0.16 g,
Water: 7.67 mL
The specific preparation steps are as follows:
0.12 g of HPMC E5, 2.05 g of Poloxamer P407 and 0.16 g of Poloxamer P188 were added to a glass container containing the compound of formula (I); finally, 7.67 mL of water was added thereto and the resulting mixture was stirred overnight at 2 to 8° C. to obtain a homogeneous suspension.

Test Example 1: Pharmacodynamic Study of Prescription 9 on Newborn New Zealand Rabbit Cataract Model Induced by Sodium Selenite 1. Experimental Animals Newborn New Zealand rabbits, aged P7 days, conventional grade, 5 young rabbits in each nest with one mother rabbit to nurse.

2. Grouping and Processing

The experimental young rabbits were randomly divided into 5 groups, each with 5 young rabbits.

1) Normal control group (NC): 0.25 mL of normal saline was injected subcutaneously into the neck of young rabbits on day P10, and no administration was performed after day P15.

2) Model control group (MC): sodium selenite solution (in normal saline) was injected subcutaneously into the neck of young rabbits at a dose of 20 μmol/kg body weight on day P10; after day P15, blank eye drops without drugs were dripped into the right eye for 42 consecutive days, three times a day.

3) Positive control group (PC): sodium selenite solution (in normal saline) was injected subcutaneously into the neck of young rabbits at a dose of 20 μmol/kg body weight on day P10; after day P15, Kary Uni eye drops (Japan Santen Pharmaceutical Co., Ltd) were dripped into the right eye for 42 consecutive days, three times a day.

4) Lanosterol eye drops treatment group (LT): sodium selenite solution (in normal saline) was injected subcutaneously into the neck of young rabbits at a dose of 20 μmol/kg body weight on day P10; after day P15, lanosterol eye drops were dripped into the right eye for 42 consecutive days, three times a day.

5) Prescription 9: sodium selenite solution (in normal saline) was injected subcutaneously into the neck of young rabbits at a dose of 20 μmol/kg body weight on day P10; after day P15, prescription 9 was dripped into the right eye for 42 consecutive days, three times a day.

3. Experimental Detection

1) Slit lamp photography: newborn New Zealand rabbits induced by sodium selenite were observed by slit lamp before administration, at 7 days, 14 days, 21 days and 42 days after administration;

2) In vitro lens transparency test: on the last day, the animal eyeballs were dissected, the lens containing capsule was completely isolated, and the lens was placed on a grid paper (2.12×2.12 mm); the sharpness of the grid through the lens was photographed.

3) Glutathione peroxidase (GSH-PX) activity detection: the GSH-PX activity of the isolated rabbit lens in each group was detected according to the method provided in the GSH-PX activity detection kit (Nanjing Jiancheng Bioengineering Institute). The experimental data were analyzed by One-Way ANOVA with SPSS statistical software, and the statistical difference level between groups was $p<0.05$ using LSD method for comparison.

4. Experimental Results

Figure 1:
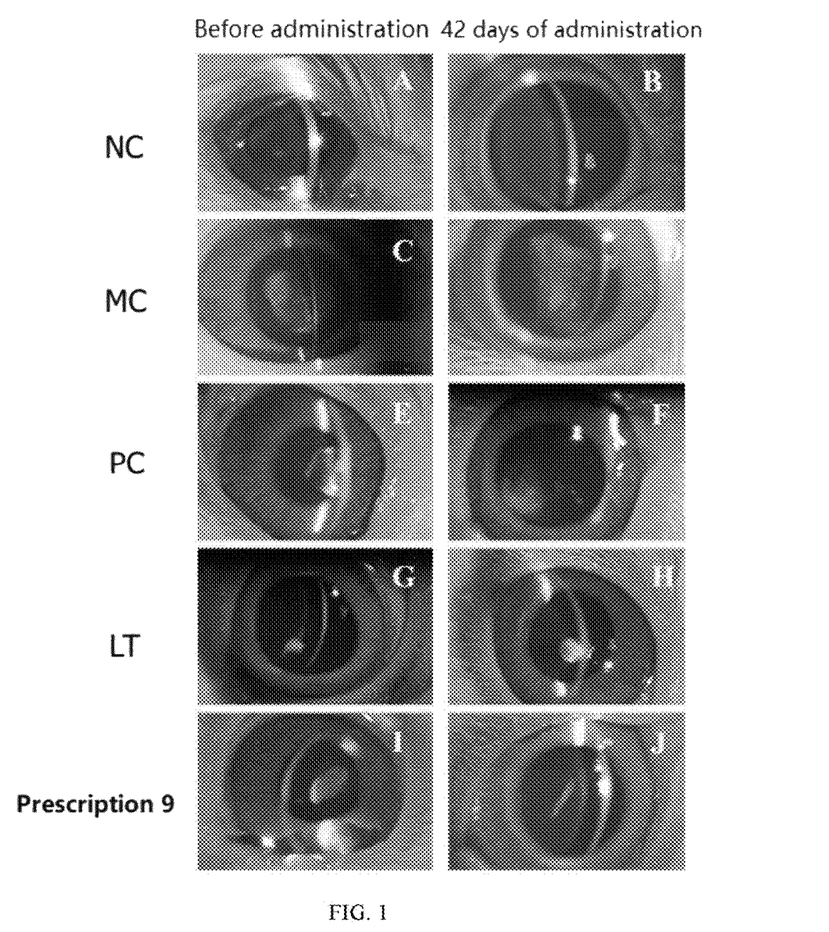
FIG. 1: The effect observed by slit lamp of prescription 9 on newborn New Zealand rabbit cataract model induced by sodium selenite. NC: Normal control group; MC: Model control group; PC: Positive control group; LT: Lanosterol eye drops treatment group.

1) Slit lamp observation: FIG. 1 shows that sodium selenite can induce cataract in the lens of newborn New Zealand rabbits. The cataract symptom was significantly alleviated at 42 days of administration of prescription 9 (FIG. 1-I) compared with the cataract symptom before administration observed by slit lamp (FIG. 1-J). However, the cataract symptom after the administration of Kary Uni eye drops (FIGS. 1-E, 1-F) and lanosterol eye drops (FIGS. 1-G, 1-H) did not change significantly compared with the symptom before administration.

Figure 2:
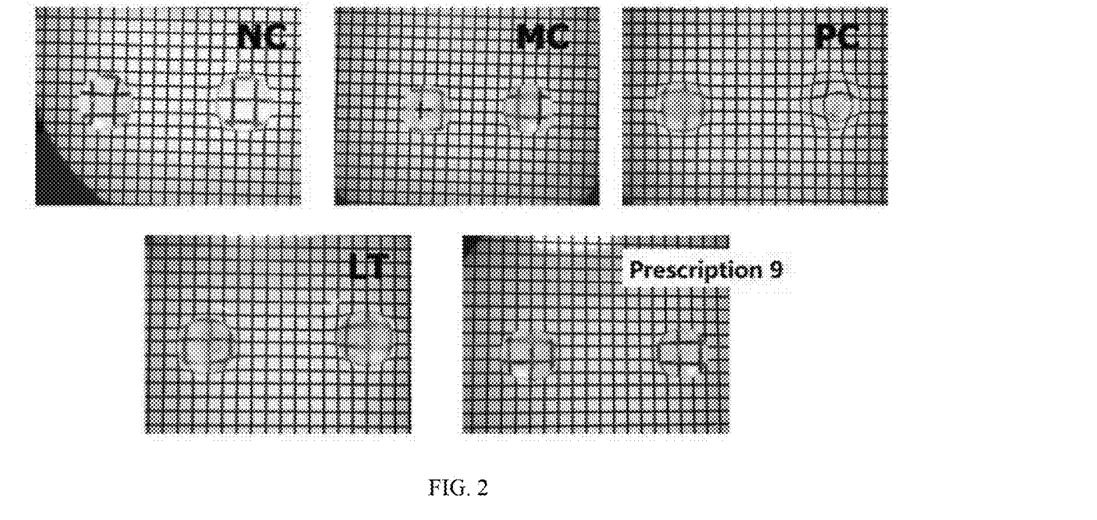
FIG. 2: Comparison of in vitro lens transparency test results of each group in the newborn New Zealand rabbit cataract model induced by sodium selenite at 42 days of administration. NC: Normal control group; MC: Model control group; PC: Positive control group; LT: Lanosterol eye drops treatment group. The grid is 2.12×2.12 mm.

2) In vitro lens transparency test: FIG. 2 shows the comparison of the lens transparency of each group in the newborn New Zealand rabbit cataract model induced by sodium selenite at 42 days after the administration. The left photo is the lens of the left eye (No drug was administered to the left eye as self-control), and the right side is the lens of the right eye (Corresponding drug was administered to the right eye according to different groups). At 42 days of the administration of prescription 9, the transparency of the right eye lens was significantly higher than that of its own left eye, and it was also significantly higher than the transparency of the lens of the MC group, but still lower than that of the NC group. The lens transparency of the right eye in the LT group did not change significantly after administration.

Figure 3:
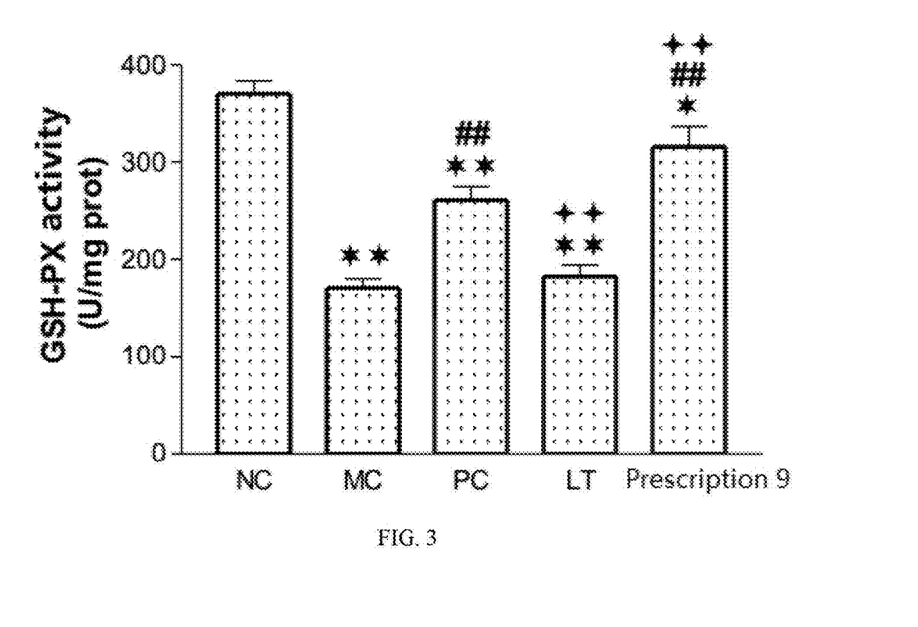
FIG. 3: Comparison of the test results of the lens glutathione peroxidase (GSH-PX) activity of each group in the newborn New Zealand rabbit cataract model induced by sodium selenite at 42 days of administration. NC: Normal control group; MC: Model control group; PC: Positive control group; LT: Lanosterol eye drops treatment group. VS NC: ** means $p<0.01$, * means $p<0.05$; VS MC: ## means $p<0.01$, # means $p<0.05$; VS PC: ++ means $p<0.01$, + means $p<0.05$.

3) GSH-PX activity detection: At 42 days of administration, the lens GSH-PX activity detection results of each group showed (see FIG. 3) that after subcutaneous injection of sodium selenite, the rabbit eye lens GSH-PX activity was significantly reduced, which was statistically different from the NC group ($p<0.01$). Prescription 9 and the positive control drug of Kary Uni eye drops can increase the lens GSH-PX activity, which is statistically different from the MC group ($p<0.01$), and the improvement effect of prescription 9 is more obvious than that of Kary Uni ($p<0.01$). The effect of lanosterol eye drops on the GSH-PX activity of the lens was significantly inferior to that of prescription 9 and Kary Uni, with no statistical difference compared with the MC group ($p>0.05$).

5. Conclusion

The above results suggest that prescription 9 can alleviate the cataract symptoms of newborn New Zealand rabbits induced by sodium selenite, increase lens transparency and lens GSH-PX activity.

Test Example 2. Pharmacodynamic Study of Prescription 9 on New Zealand Rabbits Cataract Model Induced by Ultraviolet 1. Experimental Animals A total of 25 adult New Zealand rabbits, aged 2.0-2.5 kg, conventional grade, male and female.

2. Grouping and Processing

The experimental animals were randomly divided into 5 groups, each with 5 animals.

1) Normal control group (NC): Normally raised, no administration.

2) Model control group (MC): the model was built with 313 nm ultraviolet irradiation for 24 hours, and then blank eye drops without drugs were dripped into the right eye for 42 consecutive days, three times a day.

3) Positive control group (PC): the model was built with 313 nm ultraviolet irradiation for 24 hours, and then Kary Uni eye drops (Japan Santen Pharmaceutical Co., Ltd) were dripped into the right eye for 42 consecutive days, three times a day.

4) Lanosterol eye drops treatment group (LT): the model was built with 313 nm ultraviolet irradiation for 24 hours, and then lanosterol eye drops were dripped into the right eye for 42 consecutive days, three times a day.

5) Prescription 9: the model was built with 313 nm ultraviolet irradiation for 24 hours, and then prescription 9 was dripped into the right eye for 42 consecutive days, three times a day.

3. Experimental Detection

1) Slit lamp photography: each group was observed after modeling by slit lamp before administration, at 7 days, 14 days, 21 days and 42 days of administration;

2) In vitro lens transparency test: on the last day, the animal eyeballs were dissected, the lens containing capsule was completely isolated, and the lens was placed on a grid paper (2.12×2.12 mm), the sharpness of the grid through the lens was photographed.

3) Glutathione peroxidase (GSH-PX) activity detection: the GSH-PX activity of the isolated rabbit lens in each group was detected according to the method provided in the GSH-PX activity detection kit (Nanjing Jiancheng Bioengineering Institute). The experimental data were analyzed by One-Way ANOVA with SPSS statistical software, and the statistical difference level between groups was p<0.05 using LSD method for comparison.

4. Experimental Results

Figure 4:
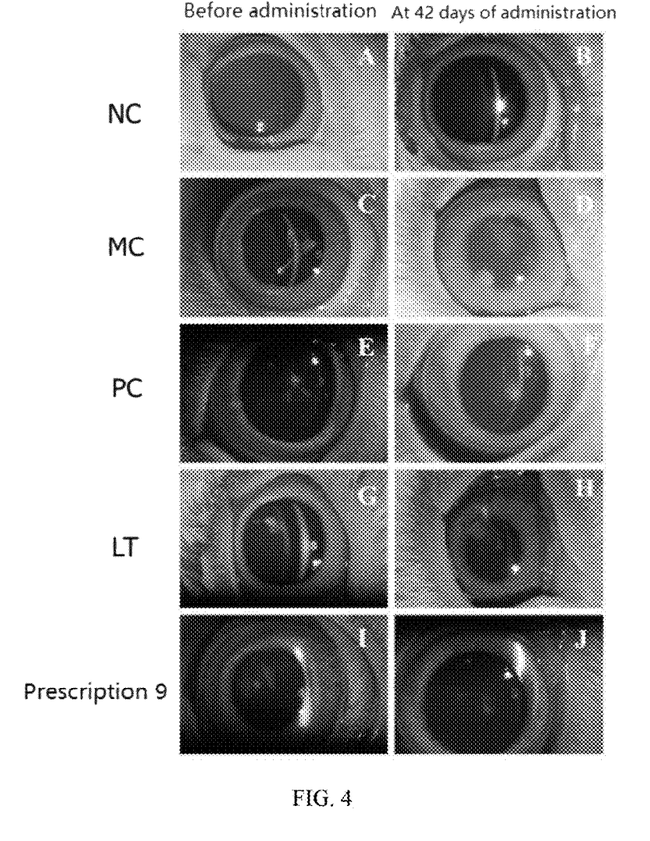
FIG. 4: The effect observed by slit lamp of prescription 9 on newborn New Zealand rabbit cataract model induced by ultraviolet. NC: Normal control group; MC: Model control group; PC: Positive control group; LT: Lanosterol eye drops treatment group.

1) Slit lamp observation: FIG. 4 shows that ultraviolet rays can induce cataract in the lens of New Zealand rabbits. The cataract symptom was significantly alleviated at 42 days of administration of prescription 9 (FIG. 4-I) compared with the cataract symptom before administration observed by slit lamp (FIG. 4-J). However, the cataract symptom after the administration of Kary Uni eye drops (FIG. 4-E, 4-F) and the lanosterol eye drops (FIG. 4-G, 4-H) did not change significantly compared with the symptom before the administration.

Figure 5:
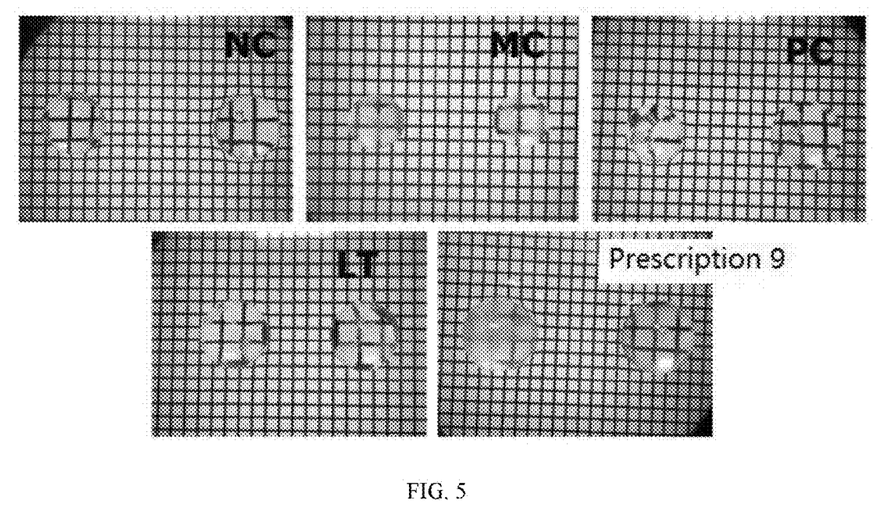
FIG. 5: Comparison of in vitro lens transparency test results of each group in the newborn New Zealand rabbit cataract model induced by ultraviolet at 42 days of administration. NC: Normal control group; MC: Model control group; PC: Positive control group; LT: Lanosterol eye drops treatment group. The grid is 2.12×2.12 mm.

2) In vitro lens transparency test: FIG. 5 shows the comparison of the lens transparency of each group in the New Zealand rabbit cataract model induced by ultraviolet rays at 42 days of administration. The left photo is the lens of the left eye (no drug was administered to the left eye as self-control), and the right photo is the lens of the right eye (corresponding drug was administered to the right eye i according to different groups). At 42 days of administration of prescription 9, the transparency of the right eye lens was significantly higher than that of its own left eye, and it was also significantly higher than the transparency of the lens of the MC group, but still lower than that of the NC group. The lens transparency of the right eye in the LT group did not change significantly after administration.

Figure 6:
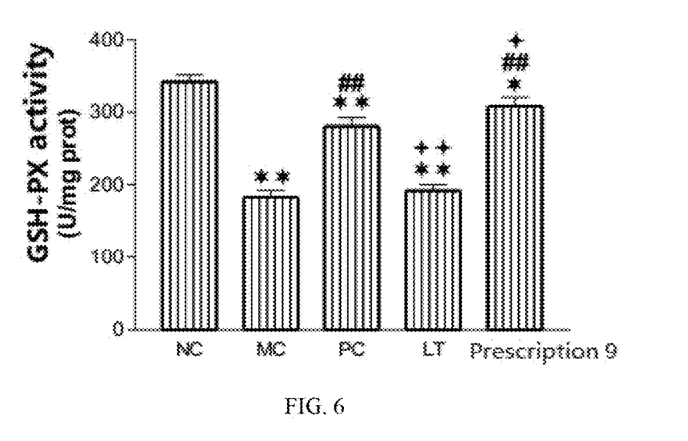
FIG. 6: Comparison of the test results of the lens glutathione peroxidase (GSH-PX) activity of each group in the newborn New Zealand rabbit cataract model induced by ultraviolet at 42 days of administration. NC: Normal control group; MC: Model control group; PC: Positive control group; LT: Lanosterol eye drops treatment group. VS NC: ** means $p<0.01$, *means $p<0.05$; V.S MC: ## means $p<0.01$, # means $p<0.05$; VS PC: ++ means $p<0.01$, + means $p<0.05$.

3) GSH-PX activity detection: At 42 days of the administration, the lens GSH-PX activity detection results of each group showed (see FIG. 6) that after ultraviolet irradiation, the rabbit eye lens GSH-PX activity was significantly reduced, which was statistically different from the NC group (p<0.01 or p<0.05). Prescription 9 and the positive control drug of Kary Uni eye drops can increase the lens GSH-PX activity, which is statistically different from the MC group (p<0.01), and the improvement effect of prescription 9 is more obvious than that of Kary Uni (p<0.05). The effect of lanosterol eye drops on the GSH-PX activity of the lens was significantly inferior to that of prescription 9 and Kary Uni, with no statistical difference compared with the MC group (p>0.05).

5. Conclusion

The above results suggest that prescription 9 can alleviate the cataract symptoms of New Zealand rabbits induced by ultraviolet irradiation, increase lens transparency and lens GSH-PX activity

What is claimed is:
1. A composition comprising a compound of formula (I) and an excipient,

2. The composition as defined in claim 1, which comprises 0.1-0.3 w/v % of the compound of formula (I).

3. The composition as defined in claim 1, wherein the excipient is one or more selected from solubilizer, pH modifier, osmotic pressure regulator, surfactant, thickener, humectant, adhesive, suspending agent, dispersant, lubricant and water.

4. The composition as defined in claim 3, wherein the solubilizer is one or more selected from HCl, polyethylene glycol 200 (PEG200), polyethylene glycol 400 (PEG400), glycerin, poloxamer 407, polyethylene oxide (PEO), sulfobutyl-β-cyclodextrin (SBE-β-CD), hydroxypropyl-β-cyclodextrin (HP-β-CD), poloxamer 188, polyvinylpyrrolidone (PVP) and Tween 80.

5. The composition as defined in claim 3, wherein the pH modifier is one or more selected from HCl, Tris-HCl, citric acid buffer and NaOH.

6. The composition as defined in claim 3, wherein the osmotic pressure regulator is one or more selected from phosphate buffered saline (PBS), sodium hyaluronate, dipotassium ethylenediaminetetraacetate (EDTA-K$_2$), and disodium ethylenediaminetetraacetate (EDTA-Na$_2$).

7. The composition as defined in claim 3, wherein the surfactant is one or more selected from Tween 80, Tween 20 and hydrogenated castor oil.

8. The composition as defined in claim 3, wherein the thickener is one or more selected from PEG200, glycerin, PEG400, poloxamer 188, poloxamer 407, PEO, polyoxyethylene castor oil, sodium hyaluronate, sodium carboxymethyl cellulose, methyl cellulose (MC), carboxymethyl cellulose (CMC), hydroxyethyl cellulose (HEC), cellulose acetate phthalate (CAP) and hydroxypropyl methyl cellulose (HPMC E5).

9. The composition as defined in claim 3, wherein the humectant is one or more selected from the group consisting of glycerin, PEG200 and PEG400.

10. The composition as defined in claim 3, wherein the adhesive is one or more selected from poloxamer 407, PEO, PVP, sodium carboxymethyl cellulose, MC, CMC, HEC, CAP and HPMC E5.

11. The composition as defined in claim 3, wherein the suspending agent is one or more selected from sodium carboxymethyl cellulose, MC, CMC, HEC, CAP, and HPMC E5.

12. The composition as defined in claim 3, wherein the dispersant is one or more selected from glycerin, PEG200 and PEG400.

13. The composition as defined in claim 3, wherein the lubricant is one or more selected from glycerin, PEG200 and PEG400.

14. The composition as defined in claim 1, which consists of:
   (1) 30.38 mg of the compound of formula (I), 1.971 mL of 0.05 mol/L HCl solution, 1 mg of EDTA-Na2, 0.808 mL of 10% Tween 80 aqueous solution, 11.8 uL of 5N NaOH aqueous solution, and 6.421 mL of water;
   (2) 30.38 mg of the compound of formula (I), 0.500 mL of PEG400, 1 mg of EDTA-Na2, 0.1 mL of PBS, 2.009 g of poloxamer 188, and 7.459 mL of water;
   (3) 30.38 mg of the compound of formula (I), 0.500 mL of 0.05 mol/L HCl aqueous solution, 0.800 mL of 10% Tween 80 aqueous solution, 0.800 mL of 10% polyoxyethylene castor oil solution, 0.080 mL of glycerin, and 7.818 mL of 0.1% sodium hyaluronate aqueous solution;
   (4) 30.38 mg of the compound of formula (I), 0.500 mL of PEG400, 1.900 g of poloxamer 188, and 7.570 mL of 0.1% sodium hyaluronate solution;
   (5) 30.38 mg of the compound of formula (I), 0.400 mL of PEG400, 0.040 mL of Tween 80, 1 mg of EDTA-K2, and 9.529 mL of 0.1% sodium hyaluronate solution;
   (6) 10 mg of the compound of formula (I), 500 mg of HP-β-CD, 0.100 mL of Tween 80, 50 mg of PVP, and 9.340 ml of water;
   (7) 10 mg of the compound of formula (I), 50 mg of sodium carboxymethyl cellulose, 50 mg of Tween 80, and 9.99 mL of water;
   (8) 10 mg of the compound of formula (I), 0.45 g of PEG400, 0.025 g of Tween 80, 0.025 g of PVP, 0.475 g of HP-β-CD, and 8.515 mL of water; or
   (9) 30.38 mg of the compound of formula (I), 0.12 g of HPMC E5, 2.05 g of poloxamer P407, 0.16 g of poloxamer P188, and 7.67 mL of water.

15. The composition as defined in claim 14, wherein, the composition is eye drops.

16. The composition as defined in claim 15, which is provided in a volume of 10 mL.

17. A method for treating cataract in a subject in need thereof, comprising administering to the subject an effective amount of the composition as defined in claim 1.

18. A method for treating cataract in a subject in need thereof, comprising administering to the subject an effective amount of the composition as defined in claim 14.

* * * * *